United States Patent
Boyev (10) Patent No.: US 7,025,785 B1
(45) Date of Patent: Apr. 11, 2006

(54) INCUS REPLACEMENT PROSTHESIS

(75) Inventor: K. Paul Boyev, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 10/905,380

(22) Filed: Dec. 30, 2004

Related U.S. Application Data (60) Provisional application No. 60/533,469, filed on Dec. 30, 2003, provisional application No. 60/535,146, filed on Jan. 8, 2004.

(51) Int. Cl.
*A61F 2/18* (2006.01)
(52) U.S. Cl. .................................... 623/10
(58) Field of Classification Search ............ 623/10; 600/25; 607/55, 57, 137
See application file for complete search history.

(56) References Cited

U.S. PATENT DOCUMENTS

| | | | |
|---|---|---|---|
| 4,281,419 A | * | 8/1981 | Treace .................... 623/10 |
| 4,728,327 A | * | 3/1988 | Gersdorff ................ 623/10 |
| 4,740,209 A | * | 4/1988 | Gersdorff ................ 623/10 |
| 5,814,104 A | | 9/1998 | Beoni |
| 6,168,625 B1 | | 1/2001 | Prescott |
| 6,203,571 B1 | | 3/2001 | Magnan et al. |
| 6,241,767 B1 | | 6/2001 | Stennert et al. |
| 6,387,128 B1 | | 5/2002 | Kurz et al. |
| 2003/0097178 A1 | | 5/2003 | Roberson et al. |
| 2003/0130734 A1 | | 7/2003 | Antonelli et al. |

FOREIGN PATENT DOCUMENTS

EP 0563767 * 10/1993
WO WO-98/16175 A1 4/1998

* cited by examiner

*Primary Examiner*—David J. Isabella
(74) *Attorney, Agent, or Firm*—Smith & Hopen, P.A.; Molly L. Sauter (57) ABSTRACT

The present invention provides a device to restore hearing to individuals who have a discontinuity in the middle ear sound conductive mechanism. The device in accordance with the present invention addresses a specific problem arising often in middle ear surgery. Currently available middle ear prostheses are inadequate to remedy the specific problem of a lateral relationship of the stapes capitulum to the malleus, thereby necessitating a cartilage graft resulting in poor sound conductive properties. The present invention provides a middle ear prosthesis that solves the problems associated with the lateral relationship of the stapes capitulum to the malleus.

17 Claims, 7 Drawing Sheets

Prior Art

Prior Art

Prior Art Devices

INCUS REPLACEMENT PROSTHESIS

CROSS REFERENCE TO RELATED APPLICATIONS

This application claims priority to U.S. Provisional Patent Application No. 60/533,469 filed Dec. 30, 2003 and U.S. Provisional Patent Application No. 60/535,146 filed Jan. 8, 2004, both filed by the same inventor and both entitled: "Promotory Anchored Incus Replacement Prosthesis."

BACKGROUND OF INVENTION

The present invention addresses a specific problem arising often in middle ear surgery. Numerous causes contribute to ossicular discontinuity including chronic ear disease, congenital aplasia and hypoplasia, and traumatic injury. The location of the incus predisposes it to damage from cholesteatoma. The long process of the incus is most frequently fractured in cases of temporal bone trauma. Additionally, the incus is the ossicle which is most likely to be congenitally hypoplastic or even absent. For the above reasons, ossicular discontinuity secondary to an incus deficiency is one of the most commonly encountered conditions requiring middle ear surgery.

Designs for incus replacement prostheses (IRPs) derive from attempts to sculpt homograft incudi into one of two configurations: the major columellar strut and the minor columellar strut. The term "columella" refers to the resemblance of the resulting ossicular connection to the avian middle ear system. The terms "major" and "minor" refer to the residual structure of the stapes, the final bone in the ossicular chain. If the superstructure of the stapes has been retained, only a small gap exists from the malleus to the capitulum of the stapes and therefore a "minor columellar strut" design can be used to bridge this gap. If the superstructure has been eroded and only the footplate of the stapes remains, a "major columellar strut" would be needed to bridge the larger gap from the malleus to the capitulum of the stapes.

Currently available middle ear prostheses are inadequate to remedy the specific problem of a lateral relationship of the stapes capitulum to the malleus, necessitating a cartilage graft, which has poor sound conductive properties.

The incus replacement prostheses designs available at present do not address two frequently encountered geometric inconveniences. The first problematic geometric relationship is that of a medialized malleus. Years of chronic eustachian tube dysfunction generate negative middle ear pressure, which predisposes ears to developing cholesteatoma. Collapse or atelectasis of the tympanic membrane induces long-term changes in the length of the tendons & ligaments of the malleus, including the tensor tympani tendon. The tendons and ligaments shorten, moving the malleus medially. The cumulative effect of this change in the position of the malleus is to narrow the space between the umbo and the promontory, such that the "head" of the incus replacement prostheses can become trapped in that narrowed space. Trapped between the umbo and promontory, no vibration of the incus replacement prostheses head is possible, and a conductive hearing loss is the result.

The second problematic geometric relationship is related to the first, but conceptually it is useful to consider it as a more lateral relationship of the stapes to the malleus. When this configuration is encountered, we lose the optimal angle required to allow the prosthesis to "stand up" on the stapes capitulum in order to contact the malleus. This can make it impossible to employ a prosthesis, and a material with poor vibratory properties, such as a cartilage graft, may become necessary. With some incus replacement prostheses, the change in the angle relationship of the stapes capitulum to the malleus may bring portions of the prosthesis into undesirable contact with the tympanic membrane, predisposing the tympanic membrane to erosion, perforation, and eventual prosthesis extrusion.

Accordingly, what is needed in the art is an improved incus replacement prosthesis that overcomes the problems associated with the incus replacement prostheses currently known in the art. It is desirable to have an incus prosthesis that accommodates changes in the lateral relationship of the stapes to the malleus and that is adjustable relative to the medial location of the malleus.

SUMMARY OF INVENTION

In accordance with the present invention is provided an apparatus to restore hearing to individuals who have a discontinuity in the middle ear sound conductive mechanism. The present invention addresses a specific problem arising often in middle ear surgery. Currently available middle ear prostheses are inadequate to remedy the specific problem of a lateral relationship of the stapes capitulum to the malleus, necessitating a cartilage graft, which has poor sound conductive properties.

In accordance with the present invention, an incus replacement prosthesis is provided that solves the problems of the prior art devices.

In accordance with an exemplary embodiment of the present invention, an auditory prosthesis adapted to be inserted into a human ear having a stapes and a tympanum is provided including an adjustable pivot element adapted to contact the stapes capitulum, a positioning element integral to the adjustable pivot element, and an anchoring device further including two anchoring legs forming a bearing surface to contact the inner wall of the tympanum, the two anchoring legs connected at a proximal end to form a wedge shaped opening to slideably receive the integrated pivot element and positioning element.

The pivot element may be fabricated of a variety of biocompatible materials as are known in the art. Additionally, the pivot element may be fabricated in a variety of shapes, having a variety of contours and solid and hollowed surfaces. Any shape of the pivot element is within the scope of the present invention such that the pivot element is capable of making pivotal contact with a stapes capitulum.

In a particular embodiment, the pivot element of the auditory prosthesis in accordance with the present invention is substantially solid.

In an additional embodiment, the auditory prosthesis includes an adjustable pivot element that is substantially cup shaped. Additionally, the pivot element is substantially cup shaped and further includes a cutaway portion resulting in a curved surface to contact a stapes capitulum of the ear.

The auditory prosthesis in accordance with the present invention is designed to be positioned such that the pivot element is in contact with the stapes capitulum. The prosthesis further includes a positioning element which is integral to the pivot element. The positioning element serves to adjustably fix the position of the pivot element within the wedge shaped end of the anchoring device. It is within the scope of the present invention that the positioning element be fabricated in a variety of forms, including a threaded screw, a fixed post having a head or cap portion, or any of a plurality of configurations that would be effective in positioning the pivot element within the wedged opening of the anchoring device.

In a particular embodiment, the positioning element includes a fixed post integral to the adjustable pivot element, the fixed post dimensioned to fit within the wedge shaped opening of the anchoring device, and a substantially disc shaped head, the head dimensioned to be larger than the fixed post such that the positioning element is substantially secured within the wedge shaped opening in the vertical direction and adjustable in the horizontal direction relative to the anchoring device.

The anchoring device of the present invention is effective is anchoring the auditory prosthesis to the inner wall of the tympanum of the ear thereby improving the lateral relationship of the stapes capitulum to the malleus. The anchoring device may be designed is a plurality of configurations. In a particular embodiment, the anchoring device includes two anchoring legs that are shaped having compound bends.

In a specific embodiment of the present invention, the two anchoring legs of the anchoring device are connected at a proximal end and extend towards a distal end. Each of the two anchoring legs further includes a substantially lateral bend at the distal end, a substantially downward bend following the lateral bend, and a substantially medial bend following the downward bend. In accordance with this embodiment, a bearing surface is established between the downward bend and the medial bend.

The auditory prosthesis of the present invention may additionally include a vibratory segment of the anchoring device. The vibratory segment of the prosthesis in accordance with the present invention is a part of the anchoring device and is fabricated to be positioned under the malleus thereby reducing the chance that the head of the prosthesis will become trapped between the umbo and the promontory due to changes in the medial positioning of the malleus.

Dimensions of the prosthesis in accordance with the present invention will vary dependent upon the application. In an exemplary embodiment, the device is approximately 4 to 5 mm in length, 2 mm in height and 3 mm in width. Additionally, the diameter of the wire used to fabricate the anchoring legs is approximately 0.009 inches. Other dimensions are within the scope of the invention.

The device may be fabricated from a variety of biocompatible materials. In a specific embodiment, the device is fabricated from titanium. The scope of the invention includes other materials having optimal characteristics of biocompatibility, malleability and stiffness effective for sound transmission.

As such, the present invention provides an improved incus replacement prosthesis that accommodates changes in the lateral relationship of the stapes to the malleus and that is adjustable relative to the medial location of the malleus.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
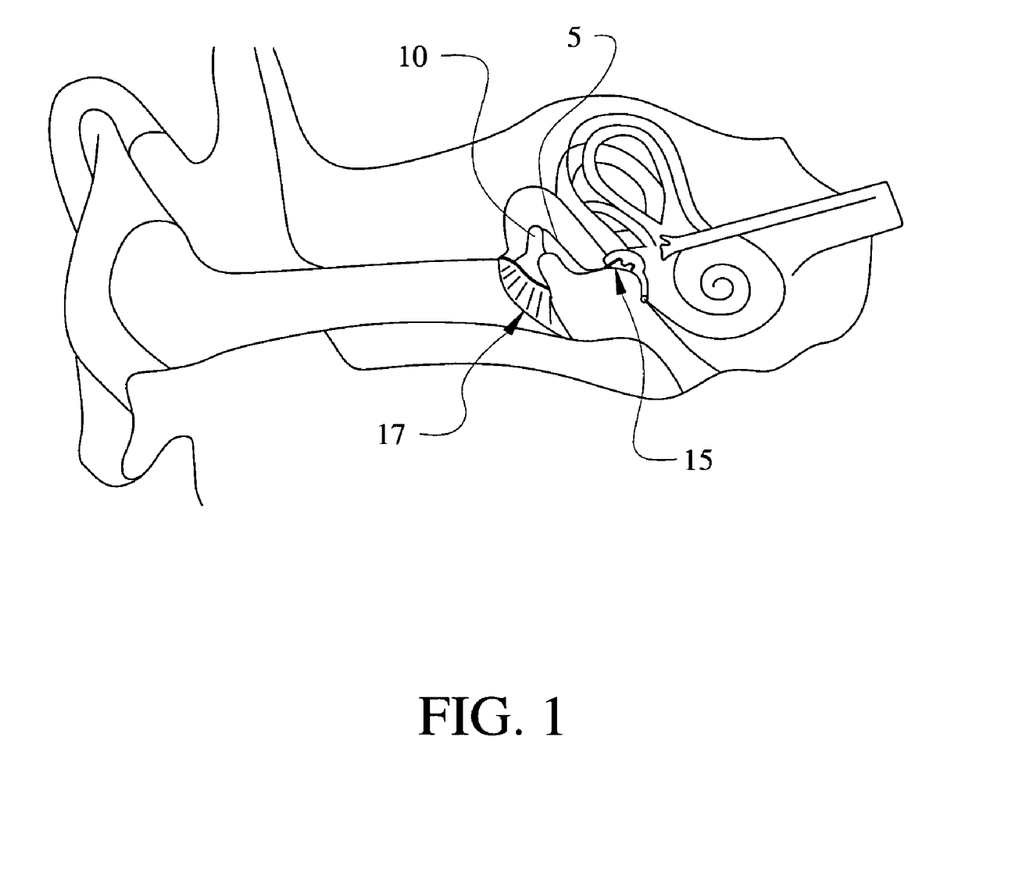
FIG. 1 is a diagram of the ear as known in the art.
Figure 2A:
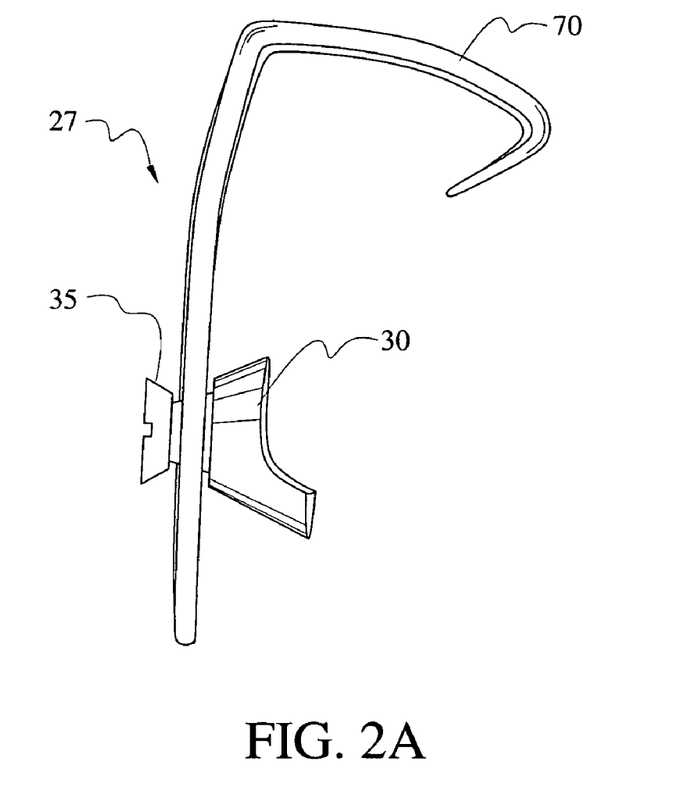
FIG. 2A is a diagrammatic side view of the prosthesis in accordance with the present invention.

In accordance with FIG. 1, a human ear is illustrated with the malleus 10, incus 5, stapes 15 and tympanic membrane 17. With reference to FIG. 2A, an exemplary embodiment of the incus replacement prosthesis 27 in accordance with the present invention is shown, including a pivotal element 30, a positioning element 35, and an anchoring device 40. A plurality of variations in design of the elements of the prosthesis are within the scope of the invention, thereby providing an improved incus replacement prosthesis that accommodates changes in the lateral relationship of the stapes to the malleus and that is adjustable relative to the medial location of the malleus.

Figure 2B:
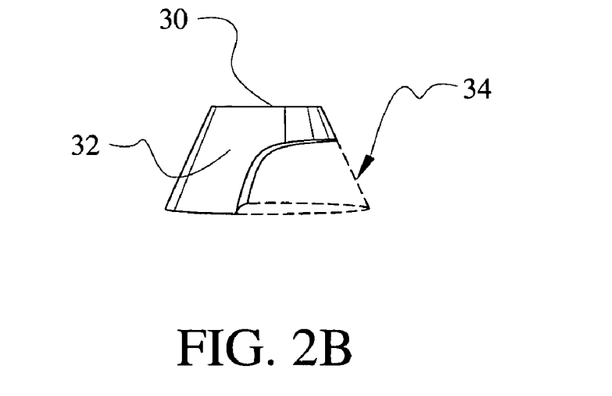
FIG. 2B is a diagrammatic view of the positioning cup in accordance with the present invention.

As illustrated with reference to FIG. 2B, the adjustable pivot element 30 may be fabricated of a solid material 32 have the shape of an upside down cup and further including a cutaway portion 34, thereby creating a curved surface upon which the pivot element is in contact with the stapes capitulum. The curved surface provides adjustable positioning of the device relative to the stapes capitulum.

FIGS. 3–6 provide illustrative view of the auditory prosthesis 27 in accordance with the present invention as viewed from a variety of angles. As shown in these exemplary embodiments, the anchoring device 40 of the prosthesis 27 further includes a pair of anchoring legs 42. The anchoring legs 42 are formed to provide a bearing surface by which to anchor the device against the inner wall of the tympanum of the ear. A variety of biocompatible materials may be used to fabricate the anchoring legs. In a particular embodiment, the legs are fabricated of titanium wherein the diameter of the wire comprising the legs is approximately 0.009 inches. Once the prosthesis is in position relative to the stapes capitulum, the anchoring device serves to anchor the prosthesis in position through contact with the inner wall of the tympanum of the ear. In the creation of this bearing surface, a plurality of configurations of the anchoring legs are within the scope of the present invention. Additionally, the anchoring legs may be fabricated from a continuous material, or fabricated separately and connected to form the anchoring device post fabrication.

Figure 3:
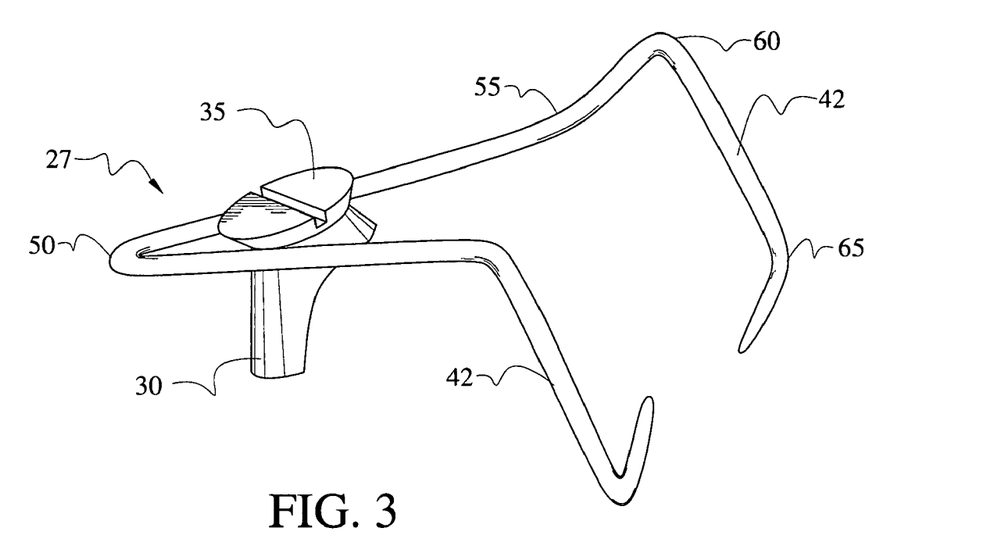
FIG. 3 is a top down diagrammatic view of the prosthesis in accordance with the present invention.
Figure 4:
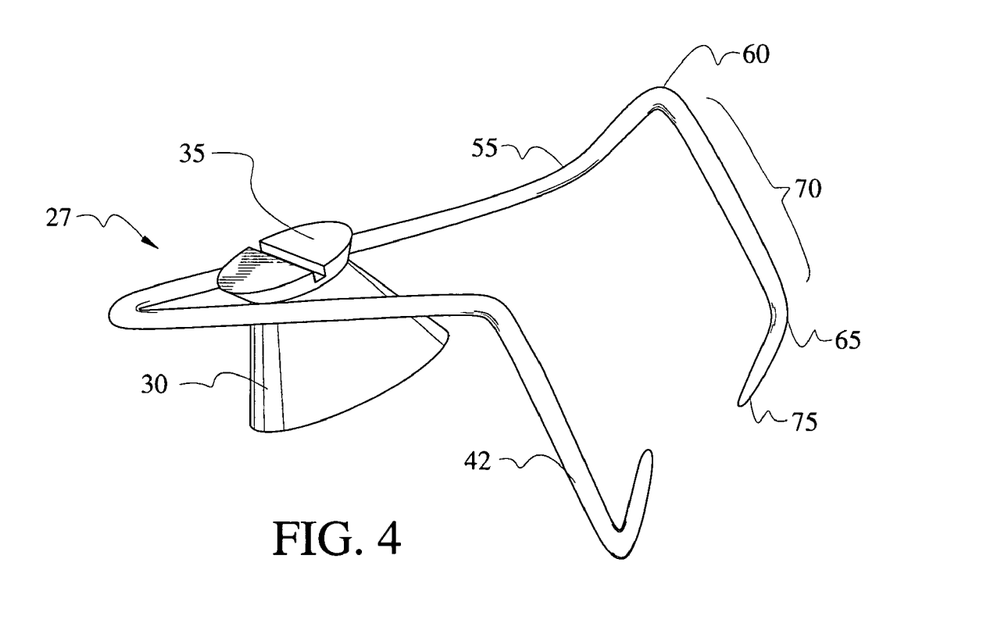
FIG. 4 is an additional top down view of the prosthesis in accordance with the present invention.
Figure 5:
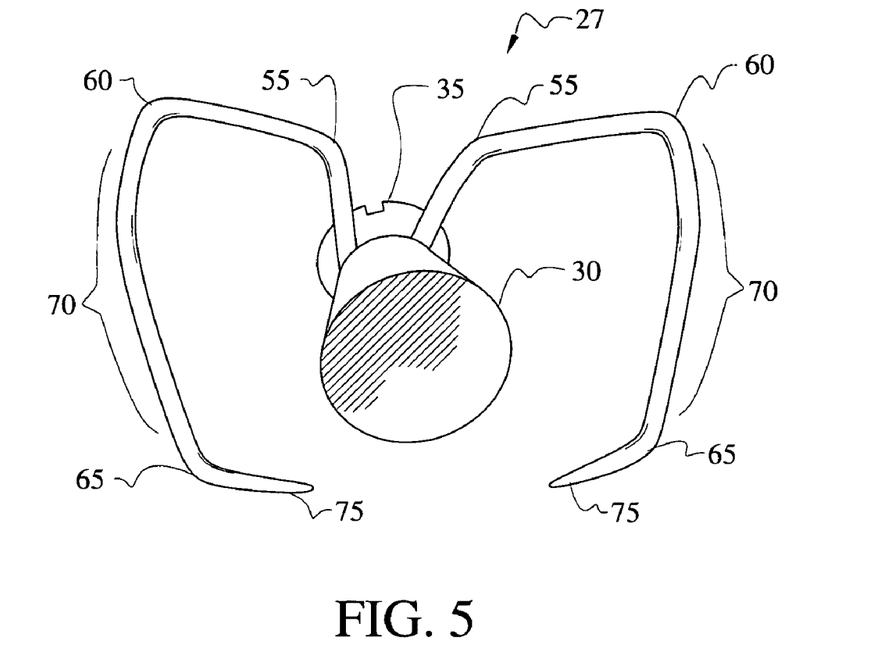
FIG. 5 is a bottom up view of the prosthesis in accordance with the present invention.
Figure 6:
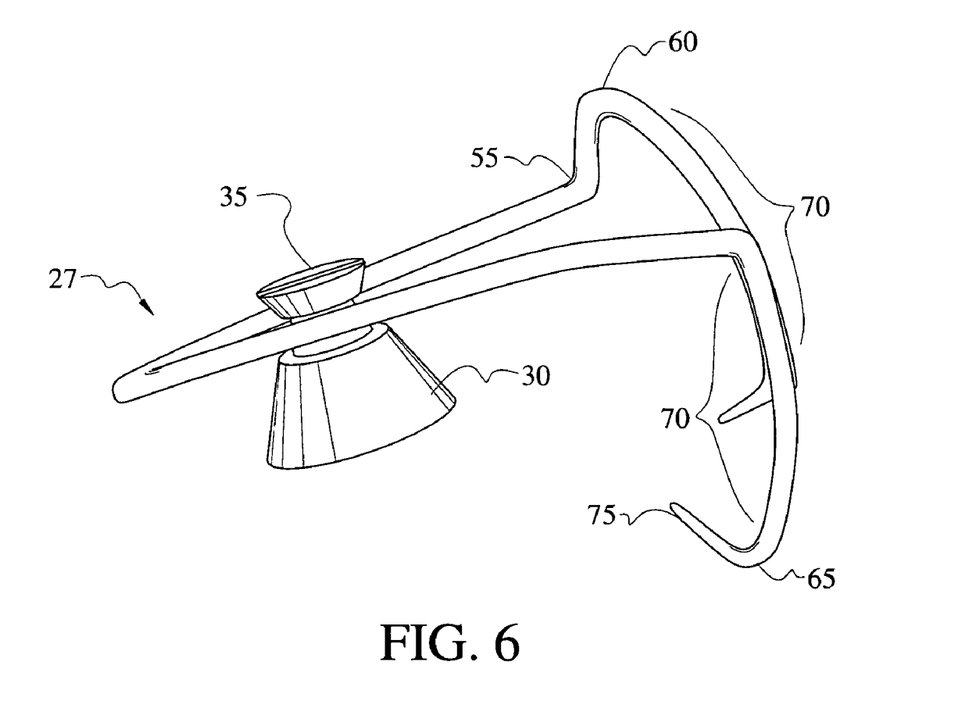
FIG. 6 is an additional side view of the prosthesis in accordance with the present invention.
Figure 7:
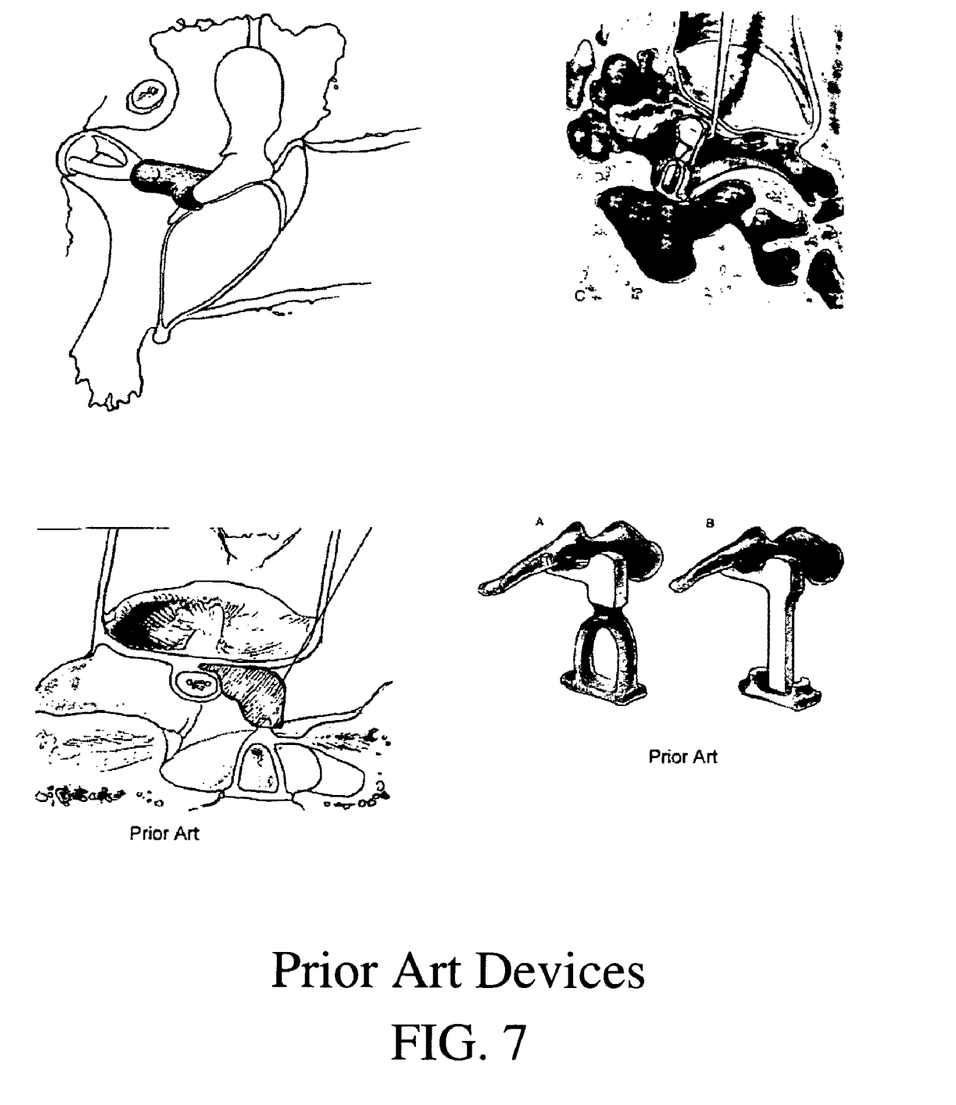
FIG. 7 is an illustration of middle ear prostheses known in the prior art.

With reference to FIG. 3, in a specific embodiment of the prosthesis, the anchoring legs 42 converge at a proximal end to form a wedge shaped opening 50. At the distal end, the legs 42 separate and form a lateral bend relative to each other 55. After the lateral bend, the legs make a downward bend 60 followed by a medial bend 65. Utilizing this configuration, a bearing surface 70 is created between the downward bend 60 of the legs and the medial bend 65.

In a additional embodiment, the portion of the anchoring legs extending beyond the medial bend 75 is positioned such as to provide a vibratory segment beneath the malleus. The vibratory segment of the prosthesis as positioned under the malleus reduces the chance that the head of the prosthesis will become trapped between the umbo and the promontory due to changes in the medial positioning of the malleus.

Figure 8A:
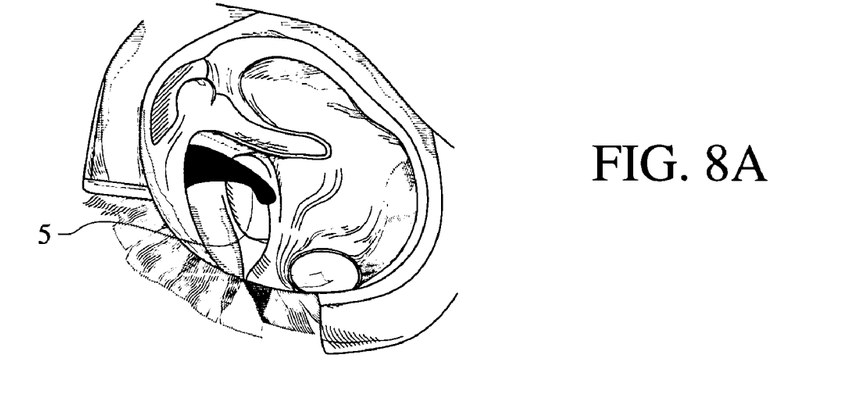
FIGS. 8A–8C is a diagrammatic view of the prosthesis in situ in accordance with the present invention.
Figure 8B:
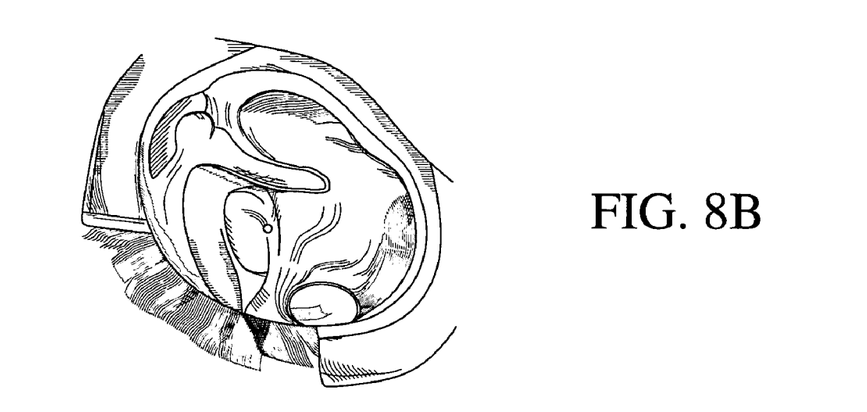
Figure 8C:
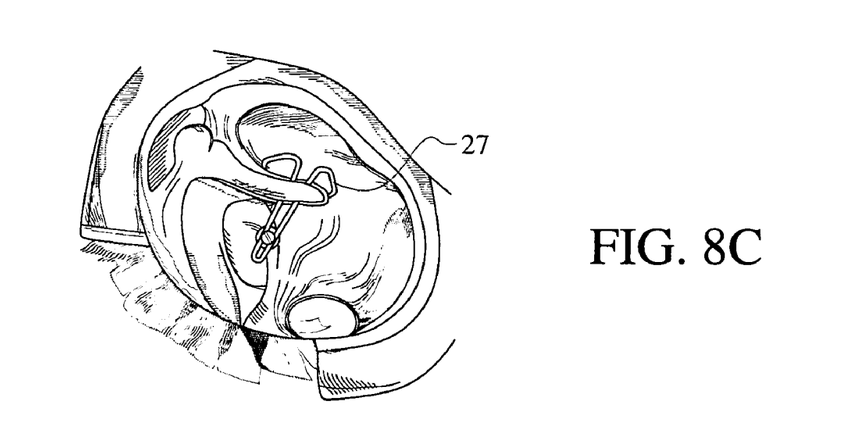

With reference to FIGS. 8A–8C, the prosthesis in accordance with the present invention is shown in situ. FIG. 8A illustrates the incus 5 of the ear as it would exist in a normal human ear. FIG. 8B illustrates the same ear, absent the incus 5. FIG. 8C illustrates the ear having the incus prosthesis 27 in accordance with the present invention as positioned in situ.

Figure 9:
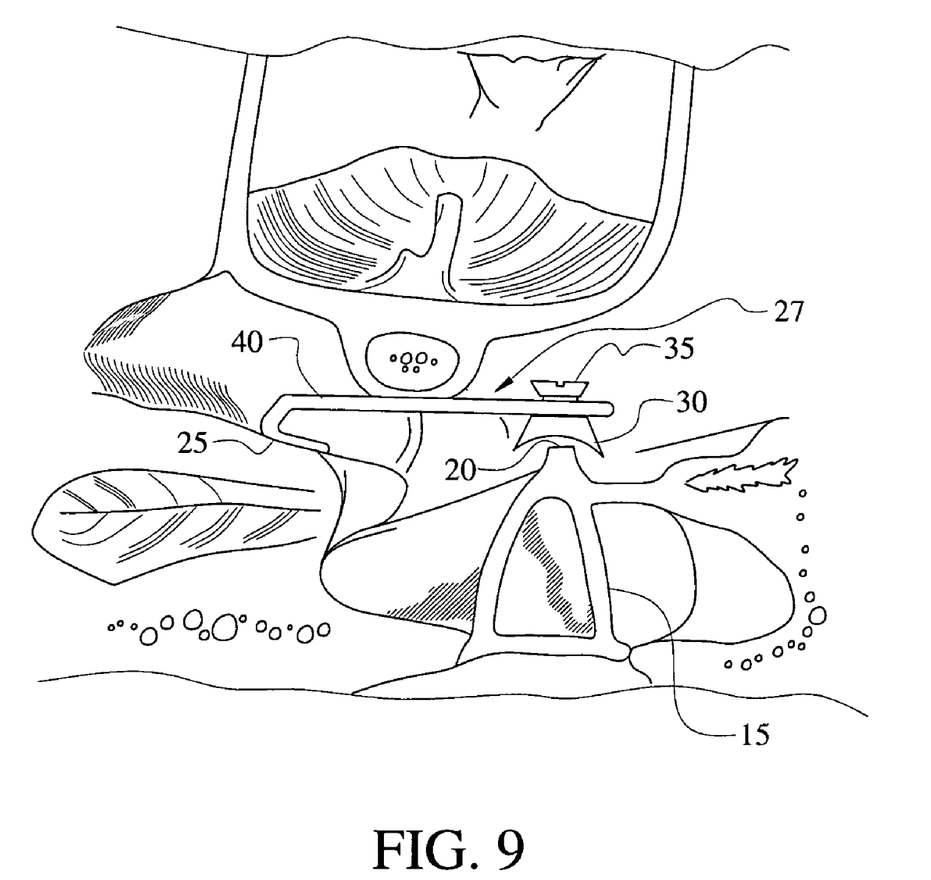
FIG. 9 is a diagrammatic view of the prosthesis in situ in accordance with the present invention.

FIG. 9 provides a more detailed view of the incus prosthesis 27 in situ. As shown, the device 27 is positioned such that the pivotal element 30 is in contact with the capitulum 20 of the stapes 15. The positioning device 35 fixes the pivotal element 30 within the wedge shaped opening of the anchoring device 40. The anchoring legs of the anchoring device serve to anchor the prosthesis against the inner wall of the tympanum 25.

It is within the scope of the present invention to expand the device to include other middle ear prostheses based upon the principle of anchoring one pivot point of a vibratory segment to the promontory. The prosthesis of the present invention would continue to be effective in the event that the vibratory properties of the suspended segment were negligible, as there would be a direct transfer of sound kinetic energy from the malleus to the stapes.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. An auditory prosthesis adapted to be inserted into a human ear having a stapes and a tympanum, the auditory prosthesis comprising:
    an adjustable pivot element adapted to contact the stapes capitulum;
    a positioning element integral to the adjustable pivot element;
    an anchoring device further comprising two anchoring legs forming a bearing surface to contact the inner wall of the tympanum, the two anchoring legs connected at a proximal end to form a wedge shaped opening to slideably receive the integrated pivot element and positioning element.

2. The auditory prosthesis of claim 1, wherein the adjustable pivot element is substantially solid.

3. The auditory prosthesis of claim 1, wherein the adjustable pivot element is substantially cup shaped.

4. The auditory prosthesis of claim 1, wherein the pivot element is substantially cup shaped having a cutaway portion resulting in a curved surface.

5. The auditory prosthesis of claim 1, wherein the positioning element further comprises a fixed post integral to the adjustable pivot element, the fixed post dimensioned to fit within the wedge shaped opening of the anchoring device, and a substantially disc shaped head, the head dimensioned to be larger than the fixed post such that the positioning element is substantially secured within the wedge shaped opening in the vertical direction and adjustable in the horizontal direction relative to the anchoring device.

6. The auditory prosthesis of claim 1, wherein the two anchoring legs are shaped having compound bends.

7. The auditory prosthesis of claim 1, wherein the two anchoring legs connected at a proximal end extend towards a distal end and each of the two anchoring legs further comprising a substantially lateral bend at the distal end.

8. The auditory prosthesis of claim 7, wherein each of the two anchoring legs further comprises a substantially downward bend following the lateral bend.

9. The auditory prosthesis of claim 8, wherein each of the two anchoring legs further comprises a substantially medial bend following the downward bend.

10. The auditory prosthesis of claim 9, wherein the bearing surface of the two anchoring legs is between the substantially downward bend and the medial bend.

11. The auditory prosthesis of claim 1, wherein the two anchoring legs connected at a proximal end extend towards a distal end and each of the two anchoring legs further comprises a substantially lateral bend at the distal end and a substantially downward bend following the lateral bend and a substantially medial bend following the downward bend.

12. The auditory prosthesis of claim 1, wherein the anchoring legs further comprise a vibratory segment positioned under a malleus of the ear.

13. The auditory prosthesis of claim 1, wherein the anchoring legs are fabricated from a titanium wire.

14. The auditory prosthesis of claim 1, wherein the anchoring legs are fabricated from a titanium wire about 0.009 inches in diameter.

15. The auditory prosthesis of claim 11, wherein the distance from the proximal end to the distal end is between about 4 mm and 5 mm.

16. The auditory prosthesis of claim 11, wherein the distance from the downward bend to the medial bend is about 2 mm.

17. The auditory prosthesis of claim 11, wherein the distance between the anchoring legs at the distal end is about 3 mm.

* * * * *